United States Patent [19]

Chen

[11] Patent Number: 5,140,022
[45] Date of Patent: Aug. 18, 1992

[54] 3-ACYCLIC OR CYCLICAMINOMETHYL-17A-LOWER-ALKYL-17A-AZA-D-HOMO-5-ALPHA-ANDROSTANES

[75] Inventor: Roger S. Chen, Edison, N.J.

[73] Assignee: Anaquest, Inc., Liberty Corner, N.J.

[21] Appl. No.: 672,726

[22] Filed: Mar. 21, 1991

Related U.S. Application Data

[63] Continuation-in-part of Ser. No. 591,340, Oct. 1, 1990, abandoned.

[51] Int. Cl.$^5$ .................. C07J 73/00; A61K 31/55; A61K 31/435
[52] U.S. Cl. .................... 514/212; 514/284; 540/597; 546/77; 544/125; 544/361
[58] Field of Search ............ 540/597; 546/77; 514/212, 284

[56] References Cited

U.S. PATENT DOCUMENTS 4,200,636  4/1980  Tuba et al. .................. 514/254

OTHER PUBLICATIONS

Anliker et al.–*Helvetica Chimica Acta*, vol. 38, No. 168, (1955) pp. 1404–1412.
Robinson et al.–*Tetrahedron*, vol. 21, (1965) pp. 743–757.
Thut et al.–*Drug Development Research*, (1985) 5:281–390.
Singh et al.–*J. Chem. Soc. Perkin I* (1974) pp. 1475–1479.
Singh et al.–*J. Chem Soc. Perkin I* (1978) pp. 305–307.
Koch–*Drugs of the Future*, vol. 8, No. 12 (1983) pp. 1025–1027.
Marshall et al.–*Eur. J. Med. Chem.-Chim. Ther.*, (1984)–19, No. 1, pp. 43–47.
Marcano et al.–*Acta Client. Venezolana* 32: (1981) pp. 296–298 (translation provided).
Greene "Protective Groups in Organic Synthesis", John Wiley & Sons, (1981), pp. 224–232.
McOmie "Protective Groups in Organic Chemistry", Plenum Press, (1973), p. 56.
March "Advanced Organic Chemistry", 3rd Addition, John Wiley & Sons, (1985), pp. 342, 346–347, 364 & 1057.
Cook et al. *J. Organic Chemistry*, vol. 33, No. 7, (1968), pp. 2789–2793.
Barton et al. "Comprehensive Organic Chemistry", vol. 2, Pergamon Press, (1979), p. 8.

*Primary Examiner*—Mukund J. Shah
*Assistant Examiner*—Philip Datlow
*Attorney, Agent, or Firm*—R. Hain Swope; Larry R. Cassett

[57] ABSTRACT

This invention pertains to novel 3-substituted-aminomethyl-3-substituted-oxy-17a-methyl-17a-lower-alkyl-17a-aza-D-homo-5-alpha-androstane compounds useful as muscle relaxants, methods for preparing such compounds, and methods for administering muscle relaxation, wherein the novel compounds are represented the general Formula:

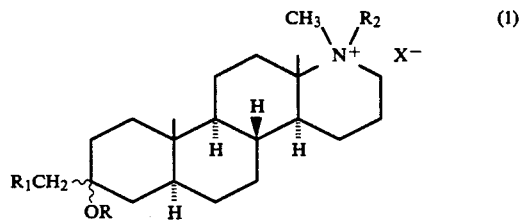

including optically active isomeric forms, and pharmaceutically acceptable acid addition salts thereof, wherein:

R is selected from the group consisting of hydrogen, lower-alkyl, lower-alkyl carbonyl, and di(lower-alkyl)amino carbonyl;

$R_1$ is selected from the group consisting of: di(lower-alkyl)substituted amino; lower-cycloalkyl lower-alkyl, lower-alkyl substituted amino;, 1-piperidinyl; 1-pyrrolidinyl; 1-hexamethyleneimino; 4-morpholinyl; 1-piperazinyl; 1-(4-methylpiperazinyl), tri(lower-alkyl)substituted amino, 1-(1-methylpiperidinyl); 1-(1-methylpyrrolidinyl); and 1-(4,4-dimethylpiperazinyl), each lower-alkyl group having from 1 to 6 carbon atoms;

$R_2$ is a lower-alkyl group having from 1 to 4 carbon atoms; and $X^-$ is a pharmaceutically acceptable anion.

11 Claims, No Drawings

3-ACYCLIC OR CYCLICAMINOMETHYL-17A-LOWER-ALKYL-17A-AZA-D-HOMO-5-ALPHA-ANDROSTANES

RELATED APPLICATIONS

This application is a continuation-in-part of U.S. patent application Ser. No. 07/591,340, filed Oct. 1, 1990, now abandoned.

This invention relates to novel 3-substituted-aminomethyl-3-substituted-oxy-17a-methyl-17a-lower-alkyl-17a-aza-D-homo-5-alpha-androstane quaternary compounds useful as skeletal muscle relaxants and pharmaceutical compositions and methods for preparing and employing such compounds. This new class of compounds possesses potent competitive neuromuscular blocking properties having a rapid onset and short period of activity.

BACKGROUND OF THE INVENTION

Many compounds such as the sedative-hypnotics and the minor and major tranquilizers produce relaxation of the skeletal muscles, but these compounds also produce other pharmacological actions which limit their utility as muscle relaxants. Relatively few classes of agents selectively act on the central nervous system to produce muscle relaxation as a primary pharmacological activity.

Succinylcholine chloride is a short acting skeletal muscle relaxant which is of the depolarizing type. Depolarizing skeletal muscle relaxants combine with cholinergic receptor sites on the motor end plate to produce depolarization which may be observed as fasciculations. Subsequent neuromuscular transmission is inhibited as long as an adequate concentration of succinylcholine remain at the receptor site.

More desirable skeletal muscle relaxants are the competitive or nondepolarizing type (curariform) which are easier to control. Nondepolarizing skeletal muscle relaxants antagonize the neurotransmitter action of acetylcholine by competitively inhibiting its binding to, and subsequently activating, cholinergic receptor sites on the motor end plate. This antagonism is inhibited, and neuromuscular block reversed, by acetylcholinesterase inhibitors such as neostigmine, edrophonium, and pyridostigmine. Examples of nondepolarizing skeletal muscle relaxants are pancuronium bromide, atracurium besylate and vecuronium bromide. The activity of these nondepolarizing skeletal muscle relaxants is, however, of intermediate duration and depolarizing skeletal muscle relaxants must be used for activity of short duration.

U.S. Pat. No. 4,200,636, issued to Tuba et al., discloses certain 3-amino-17a-aza-D-homo-5-alpha-androstane quaternary compounds said to be useful as nondepolarizing muscle relaxants having a short activity period.

SUMMARY OF THE INVENTION

This invention pertains to novel 3-substituted-aminomethyl-3-substituted-oxy-17a-methyl-17a-lower-alkyl-17a-aza-D-homo-5-alpha-androstane compounds useful as muscle relaxants, methods for preparing such compounds, and methods for administering muscle relaxation, which comprise the systemic administration to mammals of such compounds, and pharmaceutical compositions containing such compounds, wherein the novel compounds are represented by the general Formula:

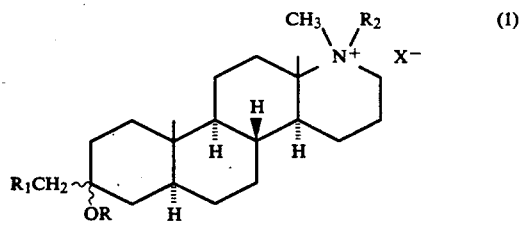

including optically active isomeric forms, and pharmaceutically acceptable acid addition salts thereof, wherein:

R is selected from the group consisting of hydrogen, lower-alkyl, lower-alkyl carbonyl, and di(lower-alkyl)amino carbonyl;

$R_1$ is selected from the group consisting of di(lower-alkyl) substituted amino; lower-cycloalkyl lower-alkyl, lower-alkyl-substituted amino; 1-piperidinyl; 1-pyrrolidinyl; 1-hexamethyleneimino; 4-morpholinyl; 1-piperazinyl, 1-(4-methylpiperazinyl); tri(lower-alkyl)substituted amino; 1-(1-methylpiperidinyl); 1-(1-methylpyrrolidinyl); and 1-(4,4-dimethylpiperazinyl), each lower alkyl group having from 1 to 6 carbon atoms;

$R_2$ is a lower-alkyl group having from 1 to 4 carbon atoms; and $X^-$ is a pharmaceutically acceptable anion.

This invention also pertains to a method for preparing the compounds represented by Formula (1) wherein $R_1$, $R_2$, and $X^-$ are as defined, and R is hydrogen and the symbol ~ represents an alpha or beta configuration, which comprises the steps:

(a) reacting a 17a-aza-D-homo-5-alpha-androstan-3-ol compound with a compound represented by the formula R'OCOHal or (R'OCO)$_2$O, wherein R' is lower-alkyl and Hal represents halide or its reactive equivalent, to form a 17a-lower-alkoxy-carbonyl-17a-aza-D-homo-5-alpha-androstan-3-ol compound;

(b) reacting the product of step (a) with an oxidizing reagent to form a 17a-lower-alkoxy-carbonyl-17a-aza-D-homo-5-alpha-androstan-3-one compound, (c) reacting the product of step (b) with a methylene ylide compound to form a (3')-spiro[oxirane-2,3'-17'a-lower-alkoxy-carbonyl-17'a-aza-D-homo-5'-alpha-androstane] compound;

(d) reacting the product of step (c) with a nitrogen-containing compound represented by the formula $R_1$-H to form a 3-substituted-aminomethyl-17a-lower-alkoxy-carbonyl-17a-aza-D-homo-5-alpha-androstan-3-ol compound;

(e) reacting the product of step (d) with a hydride reducing agent to form a 3-substituted-aminomethyl-17a-methyl-17a-aza-D-homo-5-alpha-androstan-3-ol compound, and (f) reacting the product of step (e) with an alkylating agent represented by the formula $R_2$-X to form a 3-substituted-aminomethyl-17a-methyl-17a-lower-alkyl-17a-aza-D-homo-5-alpha-androstan-3-ol quaternary salt compound.

Wherein R is other than hydrogen, the subject method additionally includes a step prior to step (f) to form a 3-substituted-oxy compound.

DETAILED DESCRIPTION OF THE INVENTION

The novel compounds of the present invention possess very desirable skeletal muscle relaxing activities. In particular, they are nondepolarizing (competitive) neuromuscular blocking agents having a rapid onset and a short period of activity. The compounds inhibit the transmission of the nervous stimulus to the transverse muscles by competitively binding with the cholinergic receptor site and antagonizing the neurotransmitter action of acetylcholine. The desirable combination of enhanced potency, rapid onset and short duration of action makes the subject compounds useful as muscle relaxants adjuncts to general anesthesia. The preferred compounds of the present invention are useful to facilitate short medical treatments such endotrachial intubation, and for skeletal muscle relaxation during surgery or mechanical ventilation.

As set out above, the muscle relaxant compounds of the present invention are quaternary ammonium salts represented by the general Formula (1):

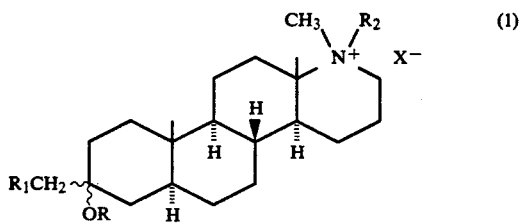

including optically active isomeric forms thereof, and pharmaceutically acceptable acid addition salts thereof, wherein R, R$_1$, R$_2$ and X$^-$ are defined as set forth below. The symbol ~ an alpha or beta configuration at the 3-position.

Group R in Formula (1) above is selected from the group consisting of hydrogen, lower-alkyl, lower-alkyl carbonyl, and di(lower-alkyl)amino carbonyl. Preferably, group R is selected from the group consisting of hydrogen and lower-alkyl carbonyl.

Group R$_1$ in Formula (1) above can be a di(lower-alkyl)substituted amine, a tri(lower-alkyl)substituted amine, or a nitrogen-containing heterocyclic ring. When R$_1$ contains a quaternary nitrogen, i.e. R$_1$ is a tri(lower-alkyl)substituted amine, 1-(1-methylpiperidinyl) and the like, the compound will contain a second pharmaceutically acceptable anion which may be the same as or different from that represented by X$^-$ in formula (1). In a preferred embodiment, R$_1$ is selected from the group consisting of: di(lower-alkyl)substituted amino; lower-cycloalkyl lower-alkyl, lower-alkyl-substituted amino; 1-piperidinyl; 1-pyrrolidinyl; 1-hexamethyleneimino; 4-morpholinyl; 1-piperazinyl; 1-(4-methylpiperazinyl); tri(lower-alkyl)substituted amino, 1-(1-methylpiperidinyl), 1-(1-methylpyrrolidinyl), and 1-(4,4-dimethylpiperazinyl). The preferred di(lower-alkyl)substituted amine is diethyl amine. The preferred lower-cycloalkyl lower-alkyl, lower alkyl-substituted amine is N-(n-propyl), N-(cyclopropylmethyl)amine. In a more preferred embodiment, R$_1$ is 1-pyrrolidinyl or 1-hexamethyleneimino.

Group R$_2$ in Formula (1) above is a straight-chain lower-alkyl group having from 1 to 4 carbon atoms, preferably methyl. Pharmaceutically acceptable anions represented by X$^-$ in Formula (1) include, for example, inorganic anions such as the chloride, bromide, sulfate, phosphate and the like, and organic anions such as the acetate, oxalate, trifluoroacetate, succinate tartrate, benezene sulfonate (besylate), methane sulfonate (mesylate), toluene sulfonate (tosylate), and the like.

A particularly preferred pharmaceutically acceptable anion in accordance with the present invention is the benzene sulfonate (besylate). The besylate is preferred, for example, because the alkylating agent utilized to prepare it, i.e. methyl benzene sulfonate, has a low vapor pressure, is considerably easier to handle than, e.g. methyl bromide which is utilized to form the bromide and which is a corrosive gas. The besylate also is advantageous, even over other preferred organic anions in terms of chemical, pharmaceutical and solution stability. Finally, the besylate is advantageous over the other salts in that it more highly crystalline. Enhanced crystallinity makes it easier to obtain a product of high purity.

In addition to the pharmaceutically acceptable anion represented by X$^-$ in Formula (1), the compounds of the present invention can form pharmaceutically acceptable acid salts where the group represented by R$_1$ does not contain a quaternary nitrogen, e.g. where R$_1$ is, e.g. di(lower-alkyl)substituted amino, 1-pyrrolidinyl 1-hexamethyleneimino, and the like. Typically, the acid from the above-listed pharmaceutically acceptable anions is utilized to form the addition salts which are prepared by conventional procedures well known to those skilled in the art.

As set out above, group —OR and group —CH$_2$R$_1$ may be in an alpha or beta configuration at the 3-position. In a preferred embodiment, group —CH$_2$R$_1$ is in the beta configuration.

The term "lower-alkyl groups", as used herein, means branched- or unbranched-hydrocarbon groups containing from 1 to 6, preferably, from 1 to 3 carbon atoms. This definition applies to the alkyl portion of lower-alkoxy groups as well. The term "lower-cycloalkyl groups", as used herein, means cyclic alkyl groups containing from 3 to 6, preferably, 3 carbon atoms. Wherein R$_1$ in Formula (1) is a nitrogen-containing heterocyclic ring, such rings may contain from 5 to 7 ring members and may include a second heteroatom, such as nitrogen or oxygen. The term "halogen", as used herein, refers to all four halogens, i.e. chlorine, fluorine, bromine and iodine, preferably bromine and iodine.

In a most preferred embodiment, the muscle relaxant compounds of the present invention are selected from the group consisting of: 3-beta-(1'-pyrrolidinylmethyl)-17a-methyl-17a-aza-D-homo-5-alpha-androstan-3-alpha-ol 17A-N-methylbenzenesulfonate; 3-beta-(1'-hexamethyleneiminomethyl)-17a-methyl-17a-aza-D-homo-5-alpha-androstan-3-alpha-ol 17a-N-methylbenzenesulfonate; 3-beta-(1'-hexamethyleneiminomethyl)-3-alpha-acetoxy-17a-methyl-17a-aza-D-homo-5-alpha-androstane 17a-N-methylbenzenesulfonate; and pharmaceutically acceptable addition salts thereof.

The compounds of the present invention can be prepared by various methods. Several convenient routes for the preparation of the inventive compounds begin with known starting materials. In one method set out in Scheme 1, the desired compounds having Formula (1) can be prepared by reacting a starting material amine of type (2) with an activated carbonate compound, such as a carbonate halide represented by the formula R'OCO-Hal or a carbonate anhydride represented by the formula (R'OCO)₂O, wherein R' is lower-alkyl and Hal is a halide or its reactive equivalent. The starting material amine (2) can be a 3-beta-ol compound or a 3-alpha-ol compound, preferably the former. The amine (2), 17a-aza-D-homo-5-alpha-androstan-3-beta-ol, can be prepared according to the procedure published by B. M. Regan and F. N. Hayes, *J. Am. Chem. Soc.*, 78, 639 (1956). R' is preferably selected from the group consisting of ethyl and tert-butyl, and more preferably is tert-butyl. Examples of halide reactive equivalents are toluene sulfonate, phenyl sulfonate, methyl sulfonate, and the like. Reaction of starting material (2) with ethyl chloroformate (ClCOOCH₂CH₃), for example, yields amide intermediate (3), 17a-ethoxycarbonyl-17a-aza-D-homo-5-alpha-androstan-3-beta-ol.

a methylene ylide. Treatment of ketone intermediate (4) with dimethyloxosulfonium methylide yields oxirane intermediate (5b), (3'R)-spiro[oxirane-2,3'-17'a-ethoxycarbonyl-17'a-aza-D-homo-5'-alpha-androstanel, wherein the methylene group is in the beta position. Treatment of ketone intermediate (4) with dimethylsulfonium methylide yields oxirane intermediate (5a), (3'S)-spiro[oxirane-2,3'-17'a-ethoxy-carbonyl-17'a-aza-D-homo-5'-alpha-androstane], wherein the methylene group is in the alpha position. Scheme 1 shows the preparation of oxirane intermediate (5b) and the corresponding 3-beta-substituted-aminomethyl derivatives. Oxirane intermediate (5a) and the corresponding 3-alpha-substituted-aminomethyl derivatives can be prepared in substantially the same manner.

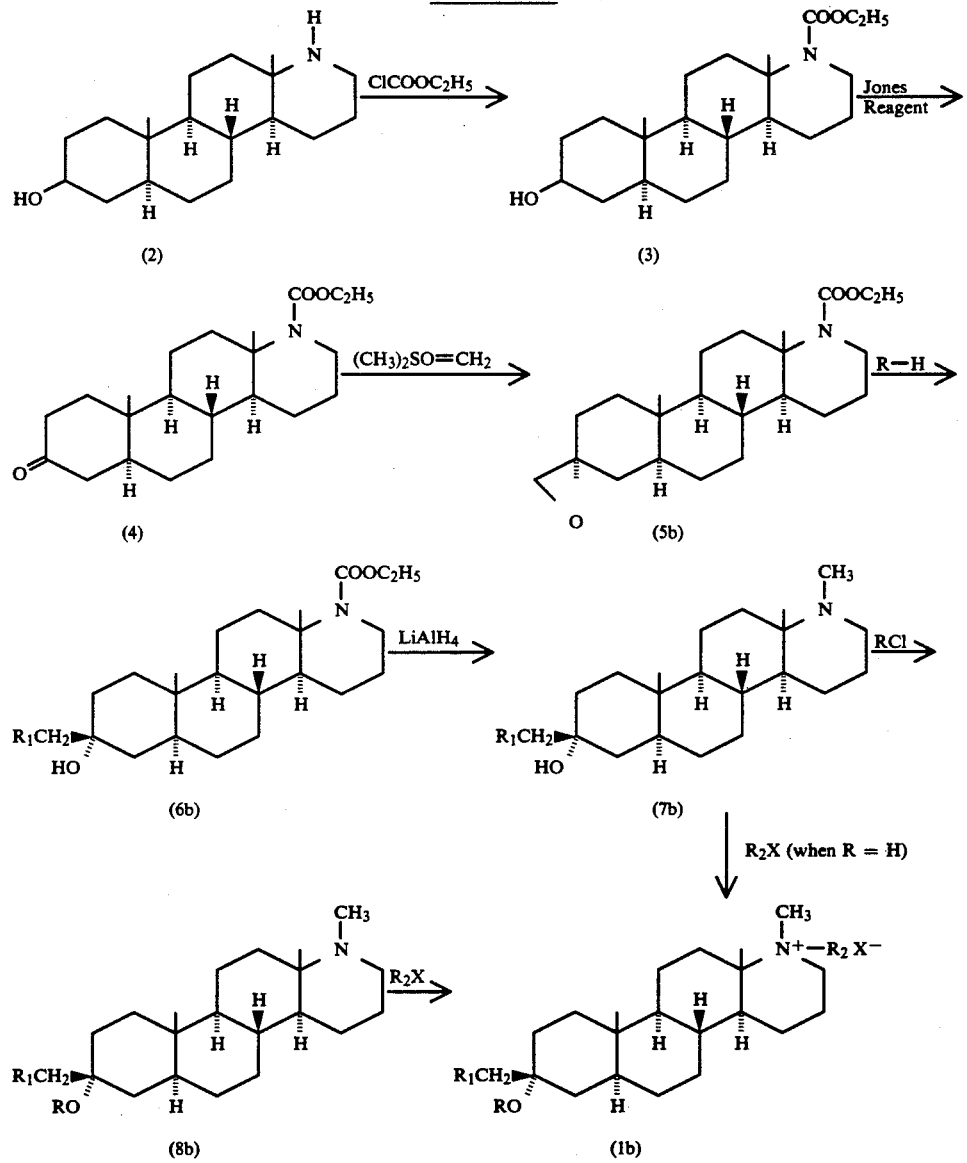

SCHEME 1

Amide intermediate (3) is then oxidized with an oxidizing reagent, such as Jones reagent or pyridinium chlorochromate, to prepare ketone intermediate (4), 17a-ethoxycarbonyl-17a-aza-D-homo-5-alpha-androstan-3-one.

Ketone intermediate (4) can then be converted into either a 3-alpha or 3-beta intermediate by reaction with As set out in Scheme 1, the desired R₁ substituent group can be introduced into oxirane intermediate (5b) by reacting intermediate (5b) with an appropriately reactive nitrogen-containing compound represented by the Formula R₁-H, wherein R₁ has the definition set out above, to obtain amine amide intermediate (6b), 3-beta- (dialkyl-substituted-aminomethyl)-17a-ethoxy-carbonyl-17a-aza-D-homo-5-alpha-androstan-3-alpha-ol. Amine amide intermediate (6b) is then reduced with a hydride reducing agent, such as lithium aluminum hydride, to provide amine intermediate (7b), 3-beta-dialkyl-substituted-aminomethyl-17a-methyl-17a-aza-D-homo-5-alpha-androstan-3-alpha-ol.

When the desired R group is hydrogen, amine intermediate (7b) can be reacted with an appropriately reactive lower-alkyl halide ($R_2$-Hal), wherein $R_2$ is defined as set out above and Hal represents a halide, to obtain compound (1b) of the present invention.

When the desired R group is other than hydrogen as defined above, i.e. R is lower alkyl, lower-alkyl carbonyl or di(lower-alkyl) amino carbonyl, amine intermediate (7b) can be reacted with a compound represented by the Formula R-Hal, wherein Hal is halogen, to introduce the desired R group at the 3-position and thereby obtain intermediate (8b), 3-beta-substituted-aminomethyl-3-alpha-R-oxy-17a-methyl-17a-aza-D-homo-5-alpha-androstane. Alternatively, amine intermediate (7b) can be reacted with a compound represented by the formula $(R)_2O$. In a preferred embodiment, amine intermediate (7b) is treated with acetyl chloride to form the acetate intermediate (8b), wherein R is $CH_3CO-$, 3-beta-substituted-aminomethyl-3-alpha-acetoxy-17a-methyl-17a-aza-D-homo-5-alpha-andro- stane.

The desired $R_2$ substituent group can then be introduced by reacting acetate intermediate (8b), R is $CH_3CO-$, with an appropriately reactive alkylating agent ($R_2$-X) such as methyl benzene sulfonate, wherein $R_2$ has the definition set out above, and wherein X is a pharmaceutically acceptable anion, to obtain compound (1b) of the present invention.

Amine intermediate (7b) or acetate intermediate (8a) can be reacted with excess alkylating agent to quaternize the $R_1$ group and the nitrogen at the 17a-position to form the diquaternary ammonium salt compounds of the present invention. Examples of quaternized $R_1$ groups are tri(lower-alkyl)substituted amino, 1-(1-methyl-piperidinyl), 1-(1-methyl-pyrrolidinyl), and 1-(4,4-dimethylpiperazinyl).

In accordance with the present invention, 3-substituted-aminomethyl-3-substituted-oxy-17a-methyl-17a-lower-alkyl-17a-aza-D-homo-5-alpha-androst ane compounds represented by the Formula:

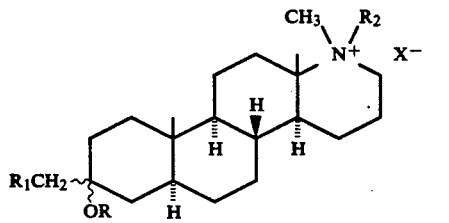

wherein $R_1$, $R_2$ and $X^-$ are as defined above, R is hydrogen, and the symbol ～ represents an alpha or beta configuration, are prepared by a method comprising the steps:

(a) reacting a 17a-aza-D-homo-5-alpha-androstan-3-ol compound with a compound represented by the formula R'OCOHal or $(R'OCO)_2O$, wherein the R' group is lower-alkyl and Hal represents a halide or its reactive equivalent, to form a 17a-lower-alkoxy-carbonyl-17a-aza-D-homo-5-alpha-androstan-3-ol compound;

(b) reacting the product of step (a) with an oxidizing reagent to form a 17a-lower-alkoxy-carbonyl-17a-aza-D-homo-5-alpha-androstan-3-one compound, (c) reacting the product of step (b) with a methylene ylide compound to form a (3')-spiro[oxirane-2,3'-17'a-lower-alkoxy-carbonyl-17'a-aza-D-homo-5'-alpha-androstane]compound;

(d) reacting the product of step (c) with a nitrogen-containing amine compound represented by the Formula $R_1$-H to form a 3-substituted-amino-methyl-17a-lower-alkoxy-carbonyl-17a-aza-D-homo-5-alpha-androstan-3-ol compound;

(e) reacting the product of step (d) with a hydride reducing agent to form a 3-substituted-aminomethyl-17a-methyl-17a-aza-D-homo-5-alpha-androstan-3-ol compound, and (f) reacting the product of step (e) with an alkylating agent represented by the Formula $R_2$-X to form a 3-substituted-aminomethyl-17a-methyl-17a-lower-alkyl-17a-aza-D-homo-5-alpha-androstan-3-ol quaternary salt compound.

Wherein R in Formula (1) is other than hydrogen, i.e. R is lower-alkyl, lower-alkyl carbonyl, or di(lower-alkyl)amino carbonyl, the method further comprises, prior to step (f), reacting the 3-substituted-aminomethyl-17a-methyl-17a-aza-D-homo-5-alpha-androstan-3-ol compound formed in step (e) with a compound represented by the formula R-Hal, wherein Hal is halogen, to form a 3-substituted-aminomethyl-3-substituted-oxy-17a-methyl-17a-lower-alkyl-17a-aza-D-homo-5-alpha-androstane compound. In another preferred embodiment, prior to step (f), the 3-substituted-aminomethyl-17a-methyl-17a-aza-D-homo-5-alpha-androstan-3-ol compound formed in step (e) is reacted with a compound represented by the formula $(R)_2O$ to form the 3-substituted-aminomethyl-3-substituted-oxy-17a-methyl-17a-lower-alkyl-17a-aza-D-homo-5-alpha-androstane compound, wherein R is selected from the group consisting of lower-alkyl carbonyl and di(lower-alkyl) amino carbonyl.

In the above reaction, it is preferred that $R^1$ be a tert-butyl group in steps (a) through (c).

As set out in Scheme 2, the desired compounds having Formula (1) can also be prepared by reacting a starting material of type (2) with an activated carbonate anhydride, such as di-tert-butyl dicarbonate, $O[COOC(CH_3)_3]_2$, to prepare amide intermediate (3'), 17a-tert-butoxycarbonyl-17a-aza-D-homo-5-alpha-androstan-3-beta-ol. Oxidation of amide intermediate (3') to ketone intermediate (4'), epoxidation of ketone intermediate (4') to oxirane intermediate (5b'), amine insertion in oxirane intermediate (5b') to form amine amide intermediate (6b'), reduction of amine amide intermediate (6b') to form amine intermediate (7b), and conversion of amine intermediate (7b) to the desired compound having Formula (1) are then carried out substantially as set out above in Scheme 1.

When $R_2$-X is reacted with intermediate (7b) or (8b) to form a monoquaternary ammonium salt, suitable solvents in which to conduct the reaction are inert organic solvents such as an aromatic hydrocarbon, a ketone such as 4-methyl-2-pentanone and the like, an ether such as 1,4-dioxane, diethylether, tetrahydofuran, 1,2-dimethoxyethane, and the like, N,N-dimethylformamide or acetonitrile. When $R_2$-X is reacted with intermediate (7b) or (8b) to form a diquaternary ammonium salt, suitable solvents in which to conduct the reaction are organic solvents such as lower-alkanols, preferably methanol. The temperature of the reaction mixture may be raised to increase the rate of reaction when appropriate.

The compounds of the present invention can be administered parenterally, i.e. by intravenous intramuscular or subcutaneous administration. Suitable pharmaceutically carriers for compositions containing the subject compounds include, for example, isotonic water, sterile water for injection (USP), alone or in combination with other solubilizing agents such as ethanol, propylene glycol, or other conventional solubilizing agents known to those skilled in the art such as Emulphor TM, CremophorEL TM, and the like. A preferred carrier is an isotonic aqueous solution of the inventive compound.

paraben; antioxidants, such as ascorbic acid or sodium metabisulfite; chelating agents, such as ethylenediaminetetraacetic acid (EDTA); buffers, such as acetates, citrates or phosphates; and agents for the adjustment of tonicity, such as sodium chloride or dextrose. The parenteral preparations may be enclosed in ampules, disposable syringes, or multiple dosage vials made of glass or plastic.

The compounds of the present invention can be administered to mammals, e.g; animals or humans, in amounts effective to provide the desired muscle relaxant therapeutic effect. Since the activity of the compounds and the degree of the desired therapeutic effect vary, the dosage level of the compound employed will also vary. The actual dosage administered will also be

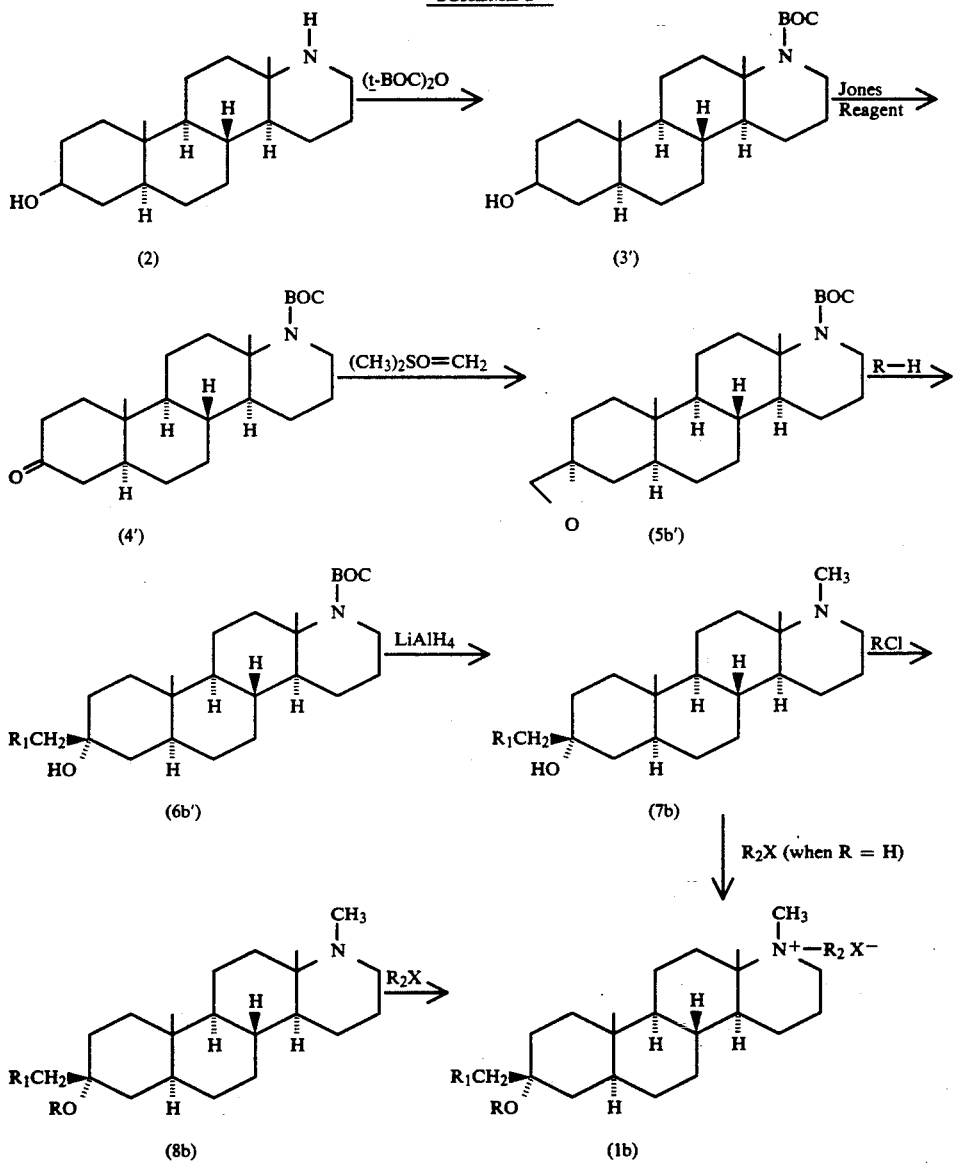

The sterile solutions or suspensions containing the subject compounds may also include the following adjuvants: a sterile diluent, such as water for injection, saline solution, fixed oils, polyethylene glycol, glycerine, propylene glycol, or other synthetic solvent; antibacterial agents, such as benzyl alcohol or methyl determined by such generally recognized factors as the body weight of the patient and the individual hypersensitiveness of the particular patient. Thus, the dosage unit for a particular patient (man) can be as low as about 0.00005 mg per kg of body weight, which the practitioner may titrate to the desired effect. It is advantageous to formulate the subject compositions in dosage unit forms for ease of administration and uniformity of dosage.

Typical parenteral compositions will contain at least about 0.1%, by weight, of the inventive compound, however, this amount may vary to between about 0.1% and 50%, by weight, of the inventive compound. The exact amount of the inventive compound present in such compositions is such that a suitable dosage unit level will be obtained. The compounds of the present invention are preferably administered intravenously and the initial dosage used will generally be in the range from about 0.2 mg to about 1.8 mg, preferably from about 0.4 mg to about 0.6 mg per kg of patient body weight. This dosage is the typical dosage necessary for an intubation procedure, and is defined as the $ED_{90}$ dosage. After this initial dosage is administered, a smaller dosage is administered intravenously either by bolus or infusion to maintain muscle relaxation during the surgical procedure. The volume for the initial dosage administered intravenously will typically be from about 3 ml to about 7 ml and this dosage volume will be injected over a time period of from about 3 seconds to about 10 seconds.

Throughout this application, various publications have been referenced. The disclosures in these publications are incorporated herein by reference in order to more fully describe the state of the art.

The present invention is further illustrated by the following examples which are presented for purposes of demonstrating, but not limiting, the preparation of the compounds and compositions of this invention.

EXAMPLE 1

This Example illustrates the preparation of the intermediate 17a-ethoxycarbonyl-17a-aza-D-homo-5-alpha-androstan-3-beta-ol (3).

Ethyl chloroformate (14.1 g, 0.13mol) was slowly added at room temperature to a stirred solution of 17a-aza-D-homo-5-alpha-androstan-3-beta-ol (2, 29.1 g, 0.1 mol) and triethylamine (15.2g, 0.15 mol) in chloroform (600 ml). After the addition was complete, the mixture was stirred at room temperature for 17 hours. The reaction mixture was washed with water (2×100 ml), aqueous hydrochloric acid (3×80 ml, 3.7% hydrochloric acid), water (2×100 ml), and dried over anhydrous sodium sulfate. The solvent was evaporated under vacuum and the residue was crystallized from ether (20 ml) and petroleum ether (50 ml) to give 27.6 g (76%) of the product 17a-ethoxycarbonyl-17a-aza-D-homo-5-alpha-androstan-3-beta-ol, (3). Melting point: 132°–134° C.

Anal. calcd. for $C_{22}H_{37}NO_3$: C, 72.69; H, 10.26; N, 3.85. Found: C, 71.86; H, 10.39; N, 3.89.

EXAMPLE 2

This Example illustrates the preparation of the intermediate 17a-ethoxycarbonyl-17a-aza-D-homo-5-alpha-androstan-3-one (4).

Jones reagent* (30 ml) was slowly added at a temperature of 5° C.–10° C. to a stirred solution of 17a-ethoxycarbonyl-17a-aza-D-homo-5-alpha-androstan-3-beta-ol from Example 1 (3, 22 g, 0.06 mol) in acetone (800 ml). The mixture was stirred at 10° C. for a period of 20 minutes, then warmed to 15° C. over another 20 minute period. The reaction mixture was then poured into cold water (4 liters). The precipitate was filtered, washed with water, and dried. The crude product was purified by column chromatography (silica gel; methylene chloride:methanol, 100:2) to give 13.3 g (61.5%) of the product 17a-ethoxycarbonyl-17a-aza-D-homo-5-alpha-androstan-3-one, (4). Melting point: 185°–187° C.

*Jones reagent was prepared by dissolving 26.72 g of chromium trioxide in 23 ml of concentrated sulfuric acid and diluting the mixture with water to a volume of 100 ml.

Anal. calcd. for $C_{22}H_{35}NO_3$: C, 73.09; H, 9.76; N, 3.87. Found: C. 72.88, H, 9,64; N, 4.00.

EXAMPLE 3

This Example illustrates another preparation of the intermediate 17a-ethoxycarbonyl-17a-aza-D-homo-5-alpha-androstan-3-one (4).

A solution of 17a-ethoxycarbonyl-17a-aza-D-homo-5-alpha-androstan-3-beta-ol from Example 1 (3, 36 g, 0.1 mol) in methylene chloride (100 ml) was added to a stirred suspension of pyridinium chlorochromate (32 g, 0.15 mol) in methylene chloride (700 ml). After being stirred for a period of 2 hours at room temperature, the mixture was diluted with ether (400 ml). The supernatant liquid was decanted and the black gummy residue was washed with ether (3×200 ml). The combined organic solutions were passed through a short pad of florisil (300 g). The solvent was evaporated under vacuum to give 33.7 g of crude product. The crude product was purified by chromatography (silica gel; methylene chloride:methanol, 100:1) to give 33.3 g (83%) of the product 17a-ethoxycarbonyl-17a-aza-D-homo-5-alpha-androstan-3-one, (4).

EXAMPLE 4

This Example illustrates the preparation of the intermediate (3'R)-spiro[oxirane-2,3'-17'a-ethoxycarbonyl-17'a-aza-D-homo-5'-alpha-androstane], (5b).

A mixture of sodium hydride (60%, 0.9 g, 0.022 mol) and trimethylsulfoxonium iodide (4.8 g, 0.022 mol) in dimethylsulfoxide (DMSO, 35 ml) was stirred for 1 hour at 25° C. to 30° C. A solution of 17a-ethoxycarbonyl-17a-aza-D-homo-5-alpha-androstan-3-one from Example 2 (4, 4 g, 0.011 mol) in tetrahydrofuran (THF, 50 ml) was added to the mixture and the resulting mixture was stirred at room temperature for 17 hours. The mixture was warmed to 50° C. for one hour, then cooled. The mixture was poured into ice water (200 ml) and extracted with ethyl acetate (4×50 ml). The organic layer was washed with water (3×50 ml) and dried over anhydrous sodium sulfate. The solvent was removed under vacuum and the residue was crystallized from petroleum ether (50 ml) to give 3.5 g (85%) of white solid product (3'R)-spiro[oxirane-2,3'-17'a-ethoxycarbonyl-17'a-aza-D-homo-5'-alpha-androstane], (5b). Melting point: 169°–70° C.

Anal calcd. for $C_{23}H_{37}NO_3$: C, 73.56; H, 9.93; N, 3.73. Found: C, 73.10; H, 9.90; N, 3.83.

EXAMPLE 5

This Example illustrates the preparation of the intermediate 3-beta-(1'-hexamethyleneiminomethyl)-17a-ethoxycarbonyl-17a-aza-D-homo-5-alpha-androstan-3-alpha-ol, (6b).

A mixture of (3'R)-spiro[oxirane-2,3'-17'a-ethoxycarbonyl-17'a-aza-D-homo-5'-alpha-androstane] from Example 4 (5b, 1.5 g, 0.004 mol), hexamethyleneimine (15 ml) and water (4 ml) was heated to reflux for 70 hours under nitrogen. The mixture was concentrated under vacuum and the residue was dissolved in methylene chloride (150 ml). The methylene chloride solution was washed with water (3×40 ml) and dried over anhydrous potassium carbonate. The solvent was removed under vacuum and the residue was purified by chromatography (silica gel; ethyl acetate:methanol, 100:2) to give 1.5 g (79%) of product 3-beta-(1'-hexamethyleneimino-methyl)-17a-ethoxycarbonyl-17a-aza-D-homo-5-alpha-androstan-3-alpha-ol, (6b). Melting point: 115°–117° C.

Anal. Calcd. for $C_{28}H_{50}N_2O_3$: C, 73.73, H, 10.62; N, 5.88. Found: C, 73.36; H, 10.62; N, 5.88.

EXAMPLE 6

This Example illustrates the preparation of the intermediate 3-beta-(1'-hexamethyleneiminomethyl)-17a-methyl-17a-aza-D-homo-5-alpha-androstan-3-alpha-ol, (7b).

A solution of 3-beta-(1'-hexamethyleneiminomethyl)-17a-ethoxycarbonyl-17a-aza-D-homo-5-alpha-androstan-3-alpha-ol from Example 5 (6b, 1.4 g, 0.0029 mol) in tetrahydrofuran (30 ml) was added slowly to a stirred suspension of lithium aluminum hydride (0.25 g) in tetrahydrofuran (30 ml) in an ice bath. After the addition was complete, the mixture was heated to reflux for 2.5 hours. The mixture was then cooled in an ice bath, and water (0.25 ml), aqueous sodium hydroxide solution (0.25 ml, 15% sodium hydroxide), and water (0.75 ml) were added sequentially with vigorous stirring. The lithium salts were removed by filtration and the organic solution was dried over anhydrous potassium carbonate. The solvent was removed under vacuum and the residue was crystallized from hexane to give 1.2 g (100%) of the product 3-beta-(1'-hexamethyleneiminomethyl)-17a-methyl-17a-aza-D-homo-5-alpha-androstan-3-alpha-ol, (7b). Melting point: 125°–128° C.

Anal. calcd. for $C_{27}H_{48}N_2O$: C, 77.83; H, 11.61; N, 6.72. Found: C, 77.82, H, 11.79; N, 6.71.

EXAMPLE 7

This Example illustrates the preparation of the intermediate 3-beta-(1'-hexamethyleneiminomethyl)-3-alpha-acetoxy-17a-methyl-17a-aza-D-homo-5-alpha-androstane,(8b).

Acetyl chloride (0.5 g) was added to a solution of 3-beta-(1'-hexamethyleneiminomethyl)-17a-methyl-17a-aza-D-homo-5-alpha-androstan-3-alpha-ol from Example 6 (7b, 0.8 g, 0.0019 mol) in methylene chloride (25 ml) and the mixture was stirred at room temperature for 17 hours. The mixture was cooled and made alkaline with concentrated ammonium hydroxide. The organic layer was washed with water (2×30 ml) and dried over anhydrous magnesium sulfate. The solvent was removed under vacuum and the residue was purified by chromatography (alumina; methylene chloride:chloroform, 1:1) to give 0.5 g (56%) of the product 3-beta-(1'-hexamethyleneiminomethyl)-3-alpha-acetoxy-17a-methyl-17a-aza-D-homo-5-alpha-androstane, (8b). Melting point: 133°–136° C.

Anal. calcd. for $C_{29}H_{50}N_2O_2$: C, 75.93; H, 10.99, N, 6.11. Found: C, 75.65, H, 11.18; N, 6.05.

EXAMPLE 8

This Example illustrates the preparation of a 3-beta-substituted aminomethyl compound of the present invention, 3-beta-(1'-hexamethyleneiminomethyl)-3-alpha-acetoxy-17a-methyl-17a-aza-D-homo-5-alpha-androstane 17a-N-methoiodide, Iodomethane (0.8 g) was added to a stirred solution of 3-beta-(1'-hexamethyleneiminomethyl)-3-alpha-acetoxy-17a-methyl-17a-aza-D-homo-5-alpha-androstane from Example 7 (8b, 0.5 g) in diethyl ether (50 ml) at room temperature and stirred for 3 days. The precipitate was collected and dried to give 0.52 g (86%) of the product 3-beta-(1'-hexamethyleneiminomethyl)-3-alpha-acetoxy-17a-methyl-17a-aza-D-homo-5-alpha-androstane 17a- N-methoiodide, (1b). Melting point: 239°–241° C.

Anal calcd. for $C_{30}H_{53}N_2O_2I$: C, 59.99, H, 8.89, N, 4.66. Found: C, 59.76.H, 8.89, N, 4.58.

EXAMPLE 9

This Example illustrates the preparation of the compound of Example 8 in the form of the besylate salt.

Methyl benzenesulfonate (4.5 g, 0.026 mol) was added to a stirred solution of 3-beta-(1'-hexamethyleneiminomethyl)-3-alpha-acetoxy-17a-methyl-17a-aza-D-homo-5-alpha-androstane (2.2 g, 0.0048 mol) in diethylether (60 ml) at room temperature and stirred for six days. The precipitate was collected and washed with diethyl ether. The crude product was dissolved in $CH_2Cl_2$ (10 ml) and filtered into diethyl ether (100 ml). The precipitate was collected and dried to give 2.6 g (86%) of 3-beta-(1'-hexamethylene-iminomethyl)-3-alpha-acetoxy-17a-methyl-17a-aza-D-homo-5-alpha androstane 17a-N-methylbenzene sulfonate, melting point: 219°–221° C.

Anal. calcd. for $C_{36}H_{58}N_2O_5S$: C, 68.53; H, 9.27; N, 4.44. Found: C, 68.42; H, 9.22; N, 4.52.

EXAMPLE 10

This Example illustrates the preparation of a 3-beta substituted aminomethyl compound of the present invention, 3-beta-(1'-pyrrolidinyl methyl)-17a-methyl-17a-aza-D-homo-5-alpha-androstan-3-alpha-ol 17a-N-methoiodide, (1b).

Iodomethane (4.9 g, 0.035 mol) was added to a stirred solution of 3-beta-(1'-pyrrolidinylmethyl)-17a-methyl-17a-aza-D-homo-5-alpha-androstan-3-alpha-ol (7b, 4.5 g, 0.0116 mol), prepared in the same manner as the intermediate from Example 6, in diethyl ether (450 ml) at room temperature. The resulting solution was stirred at room temperature for four days. The precipitate was collected and dried to give 4.6 g of crude product which was purified by chromatography (alumina; methylene chloride:methanol, 100:1) to give 3.5 g (58%) of the product 3-beta-(1'-pyrrolidinylmethyl)-17a-methyl-17a-aza-D-homo-5-alpha-androstan-3-alpha-ol 17a-N-methoiodide, (1b). Melting point: 238°–241° C.

Anal calcd. for $C_{26}H_{47}N_2OI$: C, 58.86; H, 8.93; N, 5.28. Found: C, 58.83; H, 8.87, N, 5.01.

EXAMPLE 11

This Example illustrates the preparation of the intermediate (3'S)-spiro[oxirane-2,3'-17'a-ethoxycarbonyl-17'a-aza-D-homo-5'-alpha-androstane], (5a).

A mixture of dry dimethyl sulfoxide (DMSO, 100 ml) and sodium hydride (60%, 6.4 g, 0.16 mol) was stirred at 60° C. for one hour under nitrogen. The mixture was cooled and tetrahydrofuran (THF, 250 ml) was added. A solution of trimethylsulfonium iodide (32.4 g, 0.16 mol) in dimethyl sulfoxide (200 ml) was added rapidly with stirring at −5° C. to 0° C. followed by a solution of 17a-ethoxycarbonyl-17a-aza-D-homo-5-alpha-androstan-3-one from Example 3 (4, 16 g, 0.0044 mol) in tetrahydrofuran (200 ml). After being stirred at −5° C.

for 2.5 hours, the mixture was warmed to room temperature and stirred overnight. The mixture was poured into ice water (1l) and extracted with methylene chloride (4×100 ml). The combined methylene chloride solutions were washed with water (3×200 ml), then dried over anhydrous sodium sulfate. The solvent was removed under vacuum to give 21 g of crude product. The crude product was recrystallized from methylene chloride (50 ml) and petroleum ether (150 ml) to give 6.8 g (40%) of the product, (3′S)-spiro[oxirane-2,3′-17′a-ethoxycarbonyl-17′a-aza-D-homo-5′-alpha-androstanel, (5a). Melting point: 166°–170° C.

Anal. calcd. for $C_{23}H_{37}NO_3$: C, 73.56; H, 9.93; N, 3.73. Found: C, 73.59, H, 9.69; N, 3.66.

EXAMPLE 12

This Example illustrates the preparation of the intermediate 3-alpha-(1′-pyrrolidinylmethyl)-17a-ethoxycarbonyl-17a-aza-D-homo-5-alpha-androstan-3-beta-ol, (6a).

A mixture of (3′S)-spiro[oxirane-2,3′-17′a-ethoxy-carbonyl-17′a-aza-D-homo-5′-alpha-androstane]from Example 10, (5a, 8 g, 0.0213 mol), pyrrolidine (90 ml) and water (23 ml) was heated to reflux for 70 hours under nitrogen gas. The mixture was concentrated under vacuum and the residue was dissolved in methylene chloride (150 ml). The methylene chloride solution was washed with water (3.40 ml) and dried over anhydrous potassium carbonate. The solvent was removed under vacuum and the residue was purified by chromatography (silica gel; ethyl acetate: methanol, 100:2) to give 8.5 g (89%) of product 3-alpha-(1′-pyrrolidinylmethyl)-17a-ethoxycarbonyl-17a-aza-D-homo-5-alpha-androstan-3-beta-ol, (6a). Melting point. 107°–109° C.

Anal. calcd. $C_{27}H_{46}N_2O_3$: C, 72.60; H, 10.38; N, 6.27. Found: C, 72.58, H, 10.50; N, 6.33.

EXAMPLE 13

This Example illustrates the preparation of the intermediate 3-alpha-(1′-pyrrolidinylmethyl)-17a-methyl-17a-aza-D-homo-5-alpha-androstan-3-betaol, (7a).

A solution of 3-alpha-(1′-pyrrolidinylmethyl)-17a-ethoxycarbonyl-17a-aza-D-homo-5-alpha-androstan-3-beta-ol from Example 12 (6a, 1.2 g, 0.0027 mol) in tetrahydrofuran (30 ml) was added slowly to a stirred mixture of lithium aluminum hydride (0.45 g, 0.011 mol) in tetrahydrofuran with cooling. After addition was complete, the mixture was heated to reflux for 2.5 hours. The mixture was then cooled in an ice bath, and water (0.45 ml), 15% sodium hydroxide (0.45 ml), and water (1.35 ml) were added sequentially with vigorous stirring. Lithium salts were filtered off and the organic solution was dried over anhydrous potassium carbonate. The solvent was removed under vacuum and the residue was crystallized form petroleum ether to give 1.0 g (100%) of the product, 3-alpha-(1′-pyrrolidinylmethyl)-17a-methyl-17a-aza-D-homo-5-alpha-androstan-3-beta-ol, (7a). Melting point: 94°–96° C.

Anal. calcd. for $C_{25}H_{44}N_2O$ 0.25H2O: C, 76.38, H, 11.41; N, 7.13. Found: C, 76.56; H, 11.30; N, 6.88.

EXAMPLE 14

This Example illustrates the preparation of a 3-alpha substituted aminomethyl compound of the present invention, 3-alpha-(1′-pyrrolidinylmethyl)-17a-methyl-17a-aza-D-homo-5-alpha-androstan-3-beta-ol 17a-N-methoiodide, (1a).

Iodomethane (1 g, 0.007 mol) was added to a stirred solution of 3-alpha-(1′-pyrrolidinylmethyl)-17a-methyl-17a-aza-D-homo-5-alpha-androstan-3-beta-ol from Example 12, (7a, 0.8 g, 0.002 mol) in diethyl ether (40 ml) at room temperature. The resulting solution was stirred at room temperature for three days. The precipitate was collected and dried to give 0.8 g of the crude product. The crude product was purified by chromatography (alumina; methylene chloride:methanol, 100:1) to yield 0.65 g (60%) of the product 3-alpha-(1′-pyrrolidinylmethyl)-17a-methyl-17a-aza-D-homo-5-alpha-androstan-3-beta-ol 17a-N-methoiodide, (1a). Melting point: 223°–226° C.

Anal. calcd. for $C_{26}H_{47}N_3OI$: C, 58,86; H, 8.93; N, 5.28. Found: C, 58.54, H, 9.22, N, 5.18.

EXAMPLE 15

This Example illustrates the preparation of a 3-beta substituted aminomethyl methobromide compound of the present invention, 3-beta-(1′-hexamethyleneiminomethyl)-3-alpha-acetoxy-17a-methyl-17a-aza-D-homo-5-al pha-androstane 17a-N-methobromide, (1b).

A solution of bromomethane in ether (2M, 45 ml) was added to a stirred solution of 3-beta-(1′-hexamethyleneiminomethyl)-3-alpha-acetoxy-17a-methyl-17a-aza-D-homo-5-alpha-androstane (8b, 1.1 g, 0.0024 mol), prepared in the same manner as the intermediate from Example 7, in diethyl ether (20 ml) at room temperature and stirred for four days. The precipitate was collected and dried to give 1.2 g (92%) of the product, 3-beta-(1′-hexamethyleneiminomethyl)-3-alpha-acetoxy-17a-methyl-17a-aza-D-homo-5-alpha-androstane 17a-N-methobromide, (1b). Melting point: 223°–227° C.

Anal. calcd. for $C_{30}H_{53}N_2O_2Br$: C, 65.08, H, 9.65, N, 5.06. Found: C, 64.78; H, 9.73; N, 4.87.

EXAMPLE 16

This Example illustrates the preparation of a 3-beta substituted aminomethyl methobromide compound of the present invention, 3-beta-(1′-hexamethyleneiminomethyl)-17a-methyl-17a-aza-D-homo-5-alpha-androstan-3-alp ha-ol 17a-N-methobromide, (1b).

A solution of bromomethane in ether (2 M, 70 ml) was added to a stirred solution of 3-beta-(1′-hexamethyleneiminomethyl)-17a-methyl-17a-aza-D-homo-5-alpha-androstan-3-alpha-ol (7%, 1.6 g, 0.0038 mol), prepared in the same manner as the intermediate from Example 6, in diethyl ether (80 ml) at room temperature and stirred for four days. The precipitate was collected and purified by chromatography (alumina, methylene chloride: methanol, 100:2) to give 1.4 g (71%) of the product, 3-beta-(1′-hexamethyleneiminomethyl)-17a-methyl-17a-aza-D-homo-5-alpha-androstan-3-alpha-ol 17a-N-methobromide, (1b). Melting point: 252°–255° C.

Anal. calcd. for $C_{28}H_{51}N_2OBr$: C, 65.73; H, 10.05: H, 5.48. Found: C, 65.89; H, 10.32, N, 5.36.

EXAMPLE 17

This Example illustrates the preparation of another 3-beta substituted aminomethyl methyl iodide compound of the present invention, 3-beta-(1′-piperidinylmethyl)-17a-methyl-17a-aza-D-homo-5-alpha-androstan-3-alpha-ol 17a-N-methoiodide, (1b).

Iodomethane (0.5 g) was added to a stirred solution of 3-beta-(1′-piperidinylmethyl)-17a-methyl-17a-aza-D-homo-5-alpha-androstan-3-alpha-ol (7b, 0.3 g), prepared in the same manner as the intermediate from Example 6, in diethyl ether (50 ml) at room temperature and stirred for 2 days. The precipitate was collected and dried to give 0.25 g (62%) of the product 3-beta-(1'-piperidinylmethyl)-17a-methyl-17a-aza-D-homo-5-alpha-androstan-3-alpha-ol 17a-N-methoiodide, (1b). Melting point: 255°-258° C.

Anal calcd. for $C_{27}H_{49}N_2OI$: C, 59.55, H, 9.07; N, 5.14. Found: C, 59.43; H, 9.02; N, 4.98.

EXAMPLE 18

This Example illustrates the preparation of a 3-beta substituted aminomethyl diquaternary ammonium salt compound of the present invention, 3-beta-[1'-(4',4',-dimethylpiperazinyl)methyl]-17a-dimethyl-17a-aza-D-homo-5-alpha-androstan-3-alpha-ol diiodide, (1b).

Iodomethane (0.4 g) was added to a stirred solution of 3-beta-[1'-(4'-methylpiperazinyl)methyl]-17a-methyl-17a-aza-D-homo-5-alpha-androstan-3-alp ha-ol (7b, 0.2 g), prepared in the same manner as the intermediate from Example 6,in methanol (20 ml) at room temperature and stirred for 2 days. The precipitate was collected and dried to give 0.16 g (48%) of the product, 3-beta-[1'-(4',4',-dimethylpiperazinyl)methyl]-17a-dimethyl-17a-aza-D-homo-5-alpha-androstan-3-alpha-ol diiodide, (1b). Melting point: 289°-291° C.

Anal. calcd. for $C_{28}H_{53}N_3OI_2$: C, 47.94, H, 7.62; N, 5.99. Found: C, 47.85; H, 7.44; N. 5.75.

EXAMPLE 19

This Example illustrates the preparation of a 3-beta substituted aminomethyl diquaternary ammonium salt compound of the present invention, 3-beta-[1'-(1'-methylpyrrolidinyl)methyl]-17a-dimethyl-17a-aza-D-homo-5-alp ha-androstan-3-alpha-ol diiodide, (1b).

Iodomethane (1 g) was added to a stirred solution of 3-beta-(1'-pyrrolidinylmethyl)-17a-methyl-17a-aza-D-homo-5-alpha-androstan-3-alpha-ol 7b, 0.3 g), prepared in the same manner as the intermediate from Example 6, in methanol (20 ml) at room temperature and stirred for two days. Ether (40 ml) was added and the precipitate was collected to give 0.5 g (96%) of the product, 3-beta-[1'-(1'-methylpyrrolidinyl)methyl]-17a-dimethyl-17a-aza-D-homo-5-alpha-androstan-3-alpha-ol diiodide, (1b). Melting point: 283°-286° C.

Anal. calcd. for $C_{27}H_{50}N_2OI_2$: C, 48.22, H, 7.49; N, 4.17. Found: C, 48.00; H, 7.51; N, 4.12.

EXAMPLE 20

Examples 20-24 illustrate the preparation of 3-beta substituted aminomethyl compounds of the present invention employing a 17a-tert-butoxy-carbonyl group. This Example illustrates the preparation of the intermediate 17a-tert-butoxycarbonyl-17a-aza-D-homo-5-alpha-androstan-3-beta-ol (3').

A solution of di-tert-butyl dicarbonate (3.3 g, 0.015 mol) in methylene chloride (20 ml) was slowly added at 0° C. to a stirred suspension of 17a-aza-D-homo-5-alpha-androstan-3-beta-ol (2, 2.9 g, 0.01 mol) and triethylamine (3 g, 0.03 mol) in methylene chloride (50 ml). After the addition was complete, the mixture was warmed to room temperature and stirred for 17 hours. The reaction mixture was washed with water (2×30 ml), 3.7% hydrochloric acid (2×30 ml), water (2×30 ml) and dried over anhydrous sodium sulfate. The solvent was evaporated under vacuum and the residue was purified by chromatography (silica gel; methylene chloride:methanol; 100:1) to give 3.6 g (92%) of the product, 17a-tert-butoxycarbonyl-17a-aza-D-homo-5-alpha-androstan-3-beta-ol (3'). Melting point. 165°-167° C.

Anal. calcd. for $C_{24}H_{41}NO_3$: C, 73.61; H, 10.55; N, 3.58. Found: C, 73.91; H, 10.70; N, 3.69.

EXAMPLE 21

This Example illustrates the preparation of the intermediate 17a-tert-butoxycarbonyl-17a-aza-D-homo-5-alpha-androstan-3-one (4').

A solution of 17a-tert-butoxycarbonyl-17a-aza-D-homo-5-alpha-androstan-3-beta-ol from Example 20 (3', 29.3 g, 0.075 mol) in methylene chloride (100 ml) was added at room temperature to a mechanically stirred suspension of pyridinium chlorochromate (24.3 g, 0.113 mol) in methylene chloride (500 ml). After the suspension was stirred two hours at room temperature, ether (300 ml) was added. The supernatant liquid was decanted and the black gummy residue was washed with ether (3×150 ml). The combined organic solutions were passed through a short pad of florisil (300 g). The solvent was removed under vacuum and the crude product was crystallized from petroleum ether to give 25 g (85%) of the product, 17a-tert-butoxycarbonyl-17a-aza-D-homo-5-alpha-androstan-3-one (4'). Melting point: 183°-185° C.

Anal. calcd. for $C_{24}H_{38}NO_3$: C, 73.99; H, 10.09, N, 3.60. Found: C, 73.76; H, 10.28, N, 3.42.

EXAMPLE 22

This Example illustrates the preparation of the intermediate (3'R)-spiro[oxirane-2,3'-17'a-tert-butoxycarbonyl-17'a-aza-D-homo-5'-alpha-androstane], (5b').

A mixture of sodium hydride (60%, 2.6 g, 0.065 mol) and trimethylsulfoxonium iodide (13.7 g, 0.062 mol) in dimethyl sulfoxide (130 ml) was stirred for one hour at 25° C. to 30 ° C. A solution of 17a-tert-butoxy-carbonyl-17a-aza-D-homo-5-alpha-androstan-3-one from Example 21 (4, 12.5 g, 0.032 mol) in tetrahydrofuran (150 ml) was added and the resulting mixture was stirred at room temperature for 17 hours. The mixture was warmed to 50° C. for one hour and then cooled. The mixture was then poured into ice water (500 ml) and extracted with methylene chloride (3×100 ml). The combined organic solutions were washed with water (3×80 ml) and dried over anhydrous sodium sulfate. The solvent was removed under vacuum and the residue was purified by chromatography (silica gel; ethyl acetate:hexane; 3:1) to give 8.5 g (66%) of the product, (3'R)-spiro[oxirane-2,3'-17'a-tert-butoxycarbonyl-17'a-aza-D-homo-5'-alpha-androstane], (5b'). Melting point: 124°-126° C.

Anal. calcd. for $C_{25}H_{41}NO_3$: C, 74.40; H, 10.24, N, 3.47. Found: C, 74.15; H, 10.05; N, 3.36.

EXAMPLE 23

This Example illustrates the preparation of the intermediate 3-beta-(1'-pyrrolidinyl)-17a-tert-butoxycarbonyl-17a-aza-D-homo-5-alpha-androstan-3-alpha-ol, (6b').

A mixture of (3'R)-spiro[oxirane-2-3'-17a-tert-butoxycarbonyl-17'a-aza-D-homo-5'-alpha-androstane]from Example 22 (5', 3 g, 0.0074 mol), pyrrolidine (26 ml) and water (6 ml) was heated to reflux for 70 hours under nitrogen. The mixture was concentrated under vacuum and the residue was dissolved in methylene chloride (100 ml). The methylene chloride solution was washed with water (3×30 ml) and dried over anhydrous potassium carbonate. The solvent was removed under vacuum and the residue was purified by chromatography (silica gel; ethyl acetate:methanol, 100:2) to give 2.7 g (7.8%) of the product, 3-beta-(1'-pyrrolidinyl)-17a-tert-butoxycarbonyl-17a-aza-D-homo-5-alpha-androstan-3-alpha-ol, (6b'). Melting point. 162°–164° C.

Anal. calcd. for $C_{29}H_{50}N_2O_3$: C, 73.37; H, 10.62; N, 5.90. Found: C, 73.31; H, 10.56; N, 5.79.

EXAMPLE 24

This Example illustrates the preparation of the intermediate 3-beta-(1'-pyrrolidinylmethyl)-17a-methyl-17a-aza-D-homo-5-alpha-androstan-3-alpha-ol, (7b).

A solution of lithium aluminum hydride in ethylene glycol dimethyl ether (0.5M, 25 ml) was added slowly to a stirred solution of 3-beta-(1'-pyrrolidinylmethyl)-17a-tert-butoxycarbonyl-17a-aza-D-homo-5-alpha-androstan-3-alpha-ol from Example 23 (6b', 2.6 g, 0.0055 mol) in ethylene glycol dimethyl ether (40 ml). After addition was complete, the mixture was heated to reflux for five hours. The mixture was then cooled in an ice bath and water (0.5 ml), 15% sodium hydroxide (0.5 ml) and water (1.5 ml) were added sequentially with vigorous stirring. The lithium salts were removed by filtration and the organic solution was dried over anhydrous potassium carbonate. The solvent was removed under vacuum and the residue was purified by chromatography (alumina; methylene chloride:methanol, 100:0.5) to give 1.4 g (68 %) of the product, 3-beta-(1'-pyrrolidinylmethyl)-17a-methyl-17a-aza-D-homo-5-alpha-androstan-3-alpha-ol, (7b). Melting point. 163°–165° C.

Anal. calcd. for $C_{25}H_{44}N_2O$: C, 77.26; H, 11.41; N, 7.21. Found: C, 77.38, H, 11.18; N, 7.18.

EXAMPLES 25–36

Further examples of 3-beta substituted aminomethyl-3-substituted-oxy-17a-methyl-17a-lower-alkyl-17a-aza-D-homo-5-alpha-androstane compounds within the scope of the present invention which were prepared by procedures analogous to those described above include:

3-beta-(1'-morpholinylmethyl)-17a-methyl-17a-aza-D-homo-5-alpha-androstan-3-alpha-ol 17a-N-methoiodide.

3-beta-(1'-piperidinylmethyl)-3-alpha-acetoxy-17a-methyl-17a-aza-D-17a-N-methoiodide.

3-beta-(1'-morpholinylmethyl)-3-alpha-acetoxy-17a-methyl-17a-aza-D-homo-5-alpha-androstane 17a-N-methoiodide.

3-beta-(1'-piperidinylmethyl)-17a-methyl-17a-aza-D-homo-5-alpha-androstan-3-alpha-ol 17a-N-methoiodide.

3-beta-(1'-hexamethyleneiminomethyl)-17a-methyl-17a-aza-D-homo-5-alpha-androstan-3-alpha-ol 17a-N-methoiodide.

3-beta-(1'-pyrrolidinylmethyl)-3-alpha-acetoxy-17a-methyl-17a-aza-D-homo-5-alpha-androstane 17a-N-methoiodide.

3-beta-(1'-pyrrolidinylmethyl)-17a-methyl-17a-aza-D-homo-5-alpha-androstan-3-alpha-ol 17a-N-methoiodide.

3-beta-(1'-hexamethyleneiminomethyl)-3-alpha-acetoxy-17a-methyl-17a-aza-D-homo-5-alpha-androstane 17a-N-methoiodide.

3-beta-diethylaminomethyl-17a-methyl-17a-aza-D-homo-5-alpha-androstan-3-alpha-ol 17a-N-methoiodide.

3-beta-diethylaminomethyl-3-alpha-acetoxy-17a-methyl-17a-aza-D-homo-5-alpha-androstane 17a-N-methoiodide.

3-beta-N-(n-propyl)-N-(cyclopropylmethyl)-aminomethyl-3-alpha-acetoxy-17a-methyl-17a-aza-D-homo-5-alpha-androstane 17a-N-methiodide.

3-beta-N-(n-propyl)-N-(cyclopropylmethyl)-aminomethyl-17a-methyl-17a-aza-D-homo-5-alpha-androstan-3-alpha-ol 17a-N-methiodide.

EXAMPLES 37–43

Examples of diquaternary ammonium salt 3-beta substituted aminomethyl-3-substituted-oxy-17a-methyl-17a-lower-alkyl-17a-aza-D-homo-5-alpha-androstane compounds within the scope of the present invention which were prepared by procedures analogous to those described above include:

3-beta-[1'-(4',4'-dimethylpiperazinyl)methyl]-17a-dimethyl-17a-aza-D-homo-5-alpha-androstan-3-alpha-ol diiodide.

3-beta-[1'-(4', 4'-dimethylpiperazinyl)methyl]-3-alpha-acetoxy-17a-dimethyl-17a-aza-D-homo-5-alpha-androstane diiodide.

3-beta-[1'-(1'-methylpiperidinyl)methyl]-3-alpha-acetoxy-17a-dimethyl-17a-aza-D-homo-5-alpha-androstane diiodide.

3-beta-[1'-(1'-methylpyrrolidinyl)methyl]-17a-dimethyl-17a-aza-D-homo-5-alpha-androstan-3-alpha-ol diiodide.

3-beta-N-methyl-N,N-diethylaminomethyl-3-alpha-acetoxy-17a-dimethyl-17a-aza-D-homo-5-alpha-androstane diiodide.

3-beta-(1'-methylpyrrolidinyl)methyl-3-alpha-acetoxy-17a-dimethyl-17a-aza-D-homo-5-alpha-androstane diiodide.

3-beta-N-methyl-N-(n-propyl)-N-(cyclopropylmethyl)aminomethyl-3-alpha-acetoxy-17a-dimethyl-17a-aza-D-homo-5-alpha-androstane diiodide.

EXAMPLES 44–52

Further examples of 3-alpha substituted aminomethyl-3-beta-substituted-oxy-17a-methyl-17a-lower-alkyl-17a-aza-D-homo-5-alpha-androstane compounds within the scope of the present invention which were prepared by procedures analogous to those described above include:

3-alpha-(1'-pyrrolidinylmethyl)-17a-methyl-17a-aza-D-homo-5-alpha-androstan-3-beta-ol 17a-N-methoiodide.

3-alpha-(1'-pyrrolidinylmethyl)-3-beta-acetoxy-17a-methyl-17a-aza-D-homo-5-alpha-androstane 17a-N-methoiodide.

3-alpha-(1'-methylpyrrolidinyl)-methyl-3-beta-acetoxy-17a-dimethyl-17a-aza-D-homo-5-alpha-androstane diiodide.

3-alpha-diethylaminomethyl-17a-methyl-17a-aza-D-homo-5-alpha-androstan-3-beta-ol 17a-N-methoiodide.

3-alpha-diethylaminomethyl-3-beta-acetoxy-17a-methyl-17a-aza-D-homo-5-alpha-androstane 17a-N-methoiodide.

3-alpha-N-methyl-N,N-diethylamino-methyl-3-beta-acetoxy-17a-dimethyl-17a-aza-D-homo-5-alpha-androstane diiodide.

3-alpha-[1'-(4', 4'-dimethylpiperazinyl)-methyl]-17a-dimethyl-17a-aza-D-homo-5-alpha-androstan-3-beta-ol diiodide.

3-alpha-[1'-(4', 4'-dimethylpiperazinyl)-methyl]-3-beta-acetoxy-17a-dimethyl-17a-aza-D-homo-5-alpha-androstane diiodide.

3-alpha-(1'-hexamethyleneiminomethyl)-3-beta-acetoxy-17a-methyl-17a-aza-D-homo-5-alpha-androstane 17a-N-methoiodide.

EXAMPLE 53

A pharmaceutical composition for parenteral muscle relaxant administration can be prepared from the following ingredients:

| COMPONENTS | AMOUNTS |
|---|---|
| 3-beta-(1'-pyrrolidinylmethyl)-3-alpha-acetoxy-17a-methyl-17a-aza-D-homo-5-alpha-androstane 17a-N-methoiodide | 1 mg |
| isotonic water | 10 liters |

Of course, other compounds of this invention such as those set out in Examples 12–23 and 24–30 may be substituted for 3-beta-(1'-pyrrolidinylmethyl)-3-alpha-acetoxy-17a-methyl-17a-aza-D-homo-5-alpha-androstane 17a-N-methoiodide with the relative amount of such other compounds in the compositions depending upon their muscle relaxant activity.

EXAMPLE 54

A number of compounds in accordance with the present invention were tested for their muscle relaxant properties. Testing for neuromuscular blocking activity followed a multidimensional, multispecies approach which began with simple assessment in mice and chicks, then proceeded with increasing complexity and completeness to clinically relevant parameters in rabbits, dogs, rats, cats, and monkeys.

The first test in mice established two important factors: efficacy and potency. Mice were injected intravenously (i.v.) with a range of doses and placed on an inclined screen. A compound was considered active if a dose of 1.7 mmol/kg caused the animal to relax its grip and slide down the screen.

Neuromuscular blocking effects were then observed in chicks. This model was used to determine if the mechanism of the block was depolarizing (e.g; succinylcholine) or nondepolarizing (e.g; d-tubocurare, pancuronium, atracurium, vecuronium). Agents which were classified as depolarizing neuromuscular blockers caused an increase in muscle tone and a head-to-heel arching of the back (i.e; opistotonis). A nondepolarizer, on the other hand, resulted in muscle relaxation and complete collapse of the animal. Only the nondepolarizing agents were tested further The rabbit paw twitch model was then used to simulate the clinical application of twitch monitoring. The technique included monitoring the "train of four" and single twitch to determine potency, onset and duration of action of the drug. Other techniques which were used to confirm the mechanism of action as nondepolarizing were the reversibility of drug action by neostigmine, and anticholinesterase, and the potentiation of the twitch response following a tetanic train of pulses. Although the rabbit paw twitch screen was time consuming, it represented a comprehensive and quantitative assessment of factors which are important to the anesthesiologist.

A similar paw twitch procedure for evaluating neuromuscular compounds was then conducted in the dog, and when warranted, in rats and cats. In this way, test compounds were compared to standards on clinically relevant parameters in at least three different species.

From these data, the clinical dose and time-action were estimated. As an extension of the animal models described, further investigation into the cardiovascular effects was conducted, initially, in dogs at three times the dose that causes 90% depression of twitch (i.e., $ED_{90}$), and then complete hemodynamics were evaluated and histamine plasma concentrations were determined at $10 \times ED_{90}$. Finally, twitch, train-of-four, and blood pressure and heart rate were monitored in monkeys at the $ED_{90}$, at $3 \times ED_{90}$, and at $10 \times ED_{90}$.

Neuromuscular blocking activity was studied in anesthetized rabbits in the following manner. Male New Zealand white rabbits weighing between 2.2 and 3.6kg were anesthetized with pentabarbital (30 mg/kg) and placed on their backs upon a 40° C. water filled temperature regulation pad. A tracheotomy was performed and the lungs were mechanically ventilated at 28 breaths per minute with room air using an open system delivering 200 ml/stroke. The ventilation procedure maintained $pCO2$ at 38 mmHg and $pO2$ at 85 mmHg. The right common carotid artery was isolated and cannulated for direct measurement of blood pressure and heart rate using a statham pressure transducer. The marginal vein of the left ear was cannulated with a 23-gauge venipuncture needle for drug and fluid administration. Nerve stimulation was provided by a pair of pin electrodes placed percutaneously near the ulnar nerve at the elbow. The right ulnar nerve was stimulated at 1 Hz, 1 pps for 0.5 msecond duration. The stimulation for the left ulnar nerve was modified so that the sequence of stimuli included a train-of-four (T4) and a tetanizing stimulus. Each foreleg was taped to a cushioned plate held in a femur clamp attached to the spinal board rack. The left central digit of each paw was connected with #4 surgical silk to a force displacement transducer (Grass FLT03G). The following parameters of neuromuscular blockade were measured.

1. Potency (ED90): the intravenous dose required to depress twitch to 10% of its control value.
2. Onset: the time from injection until 85% of the maximal drug effect is achieved.
3. Duration: time from injection until the T4 has recovered to 75% of its original value.

An eight-channel Gould 2800S polygraphy was used to record analog data. The digital portion of the data collection system was configured around an Apple 11 plus microcomputer. The measurement of dose response of skeletal muscle relaxant drugs is described in detail in "Microcomputer Use in Measuring Onset, Duration and Recovery from Non-Depolarizing Skeletal Muscle Relaxants in Rabbits", P. D. Thut et al; Drug Development Research. 5, 281 (1985), which disclosure is incorporated herein by reference.

The compounds listed in Tables 1 through 3 were tested by these procedures and found to have the activities listed in the columns on the right side of Tables 1 through 3. Table 1 shows the structure activity relationship of various 3-beta substituted aminomethyl-3-substituted-oxy-17a-methyl-17a-lower-alkyl-17a-aza-D-homo-5/alpha-androstane compounds determined by the paw twitch procedure in rabbits. Table 2 shows the same structure activity relationship determined by the paw twitch procedure in dogs. Table 3 shows the structure activity relationship of various 3-alpha substituted aminomethyl 3-substituted-oxy-17a-methyl-17a-lower-alkyl-17a-aza-D-homo-5-alpha-androstane compounds determined by the paw twitch procedure in dogs.

TABLE 1

STRUCTURE ACTIVITY RELATIONSHIP OF 3-BETA SUBSTITUTED AMINOMETHYL 3-SUBSTITUTED-OXY-17A-LOWER-ALKYL-17A-AZA-D-HOMO-5-ALPHA-ANDROSTANES IN RABBIT

| COMPOUNDS | eaDose mg/kg | 85% TW sec. | Duration min. | Recovery min. | HR % Ch | BP % Ch |
|---|---|---|---|---|---|---|
| 1. 3-beta-(1'-piperidinylmethyl)-17a-methyl-17a-aza-D-homo-5-alpha-androstan-3-alpha-ol 17a-N-methoiodide | 0.241 | 26.56 | 7.29 | 6.24 | 3.8 | −2.5 |
| 2. 3-beta-(1'-morpholinylmethyl)-17a-methyl-17a-aza-D-homo-5-alpha-androstan-3-alpha-ol 17a-N-methoiodide | 1.019 | 30.84 | 8.29 | 6.54 | 4.1 | −13.6 |
| 3. 3-beta-(1'-piperidinylmethyl)-3-alpha-acetoxy-17a-methyl-17a-aza-D-homo-5-alpha-androstane 17a-N-methoiodide | 0.296 | 33.30 | 6.65 | 5.11 | −1.2 | −13.7 |
| 4. 3-beta-(1'-pyrrolidinylmethyl)-17a-methyl-17a-aza-D-homo-5-alpha-androstan-3-alpha-ol 17a-N-methoiodide | 0.458 | 19.44 | 9.10 | 7.30 | −1.0 | −6.7 |
| 5. 3-beta-(1'-hexamethyleneiminomethyl)-17a-methyl-17a-aza-D-homo-5-alpha-androstan-3-alpha-ol 17a-N-methoiodide | 0.148 | 37.55 | 5.42 | 4.83 | 8.2 | −1.0 |
| 6. 3-beta-(1'-pyrrolidinylmethyl)-3-alpha-acetoxy-17a-methyl-17a-aza-D-homo-5-alpha-androstane 17a-N-methoiodide | 0.313 | 22.20 | 5.48 | 4.89 | 4.1 | −12.7 |
| 7. 3-beta-(1'-hexamethyleneiminomethyl)-3-alpha-acetoxy-17a-methyl-17a-aza-D-homo-5-alpha-androstane 17a-N-methoiodide | 0.197 | 39.40 | 5.84 | 5.34 | −1.0 | −1.1 |
| 8. 3-beta-[1'-(4',4'-dimethyl-piperazinyl)-methyl]-17a-dimethyl-17a-aza-D-homo-5-alpha-androstan-3-alpha-ol diiodide | 0.084 | 32.07 | 8.09 | 6.09 | 0.9 | −12.6 |
| 9. 3-beta-[1'-(4',4'-dimethyl-piperazinyl)methyl]-3-alpha-acetoxy-17a-dimethyl-17a-aza-D-homo-5-alpha-androstane diiodide | 0.155 | 31.83 | 7.63 | 6.01 | 1.1 | 1.6 |
| 10. 3-beta-diethylaminomethyl-17a-methyl-17a-aza-D-homo-5-alpha-androstan-3-alpha-ol 17a-N-methoiodide | 0.258 | 28.54 | 10.17 | 8.38 | 6.1 | −9.2 |
| 11. 3-beta-diethylaminomethyl-3-alpha-acetoxy-17a-methyl-17a-aza-D-homo-5-alpha-androstane 17a-N-methoiodide | 0.329 | 29.47 | 8.77 | 7.15 | 0.8 | −6.7 |
| 12. 3-beta-N-(n-propyl)-N-(cyclopropylmethyl)aminomethyl-3-alpha-acetoxy-17a-methyl-17a-aza-D-homo-5-alpha-androstane 17a-N-methoiodide | 0.572 | 37.31 | 6.09 | 5.56 | −2.0 | −14.0 |
| 13. 3-beta-[1'-(1'-methylpiperidinyl)-methyl]-3-alpha-acetoxy-17a-dimethyl-17a-aza-D-homo-5-alpha-androstane diiodide | 0.146 | 39.51 | 9.92 | 7.82 | 1.1 | −2.5 |
| 14. 3-beta-[1'-(1'methylpyrrolidinyl)-methyl]-17a-dimethyl-17a-aza-D-homo-5-alpha-androstane-3-alpha-ol diiodide | 0.148 | 47.80 | 10.58 | 8.92 | 1.7 | −8.7 |
| 15. 3-beta-N-(n-propyl)-N-(cyclopropyl-methyl)aminomethyl-17-a-methyl-17a-aza-D-homo-5-alpha-androstane-3-alpha-ol 17a-N-methoiodide | 0.162 | 31.73 | 10.89 | 9.60 | 3.3 | −7.4 |
| 16. 3-beta-N-methyl-N,N-diethylamino-methyl-3-alpha-acetoxy-17a-dimethyl-17a-aza-D-homo-5-alpha-androstane diiodide | 0.122 | 48.45 | 6.37 | 5.25 | 1.5 | 3.4 |
| 17. 3-beta-[1'(1'-methylpyrrolidinyl)-methyl]-3-alpha-acetoxy-17a-dimethyl-17a-aza-D-homo-5-alpha-androstane diiodide | 0.196 | 35.51 | 6.36 | 6.38 | −2.3 | −1.0 |
| 18. 3-beta-N-methyl-N-(n-propyl)-N(cyclopropylmethyl)aminomethyl-3-alpha-acetoxy-17a-dimethyl-17a-aza-D-homo-5-alpha-androstane diiodide | 0.151 | 42.97 | 9.82 | 7.01 | −0.2 | −5.0 |

TABLE 2

STRUCTURE ACTIVITY RELATIONSHIP OF 3-BETA SUBSTITUTED AMINOMETHYL 3-SUBSTITUTED-OXY-17A-LOWER-ALKYL-17A-AZA-D-HOMO-5-ALPHA-ANDROSTANES IN DOG

| COMPOUNDS | eaDose mg/kg | 85% TW sec. | Duration min. | Recovery min. | HR % Ch | BP % Ch |
|---|---|---|---|---|---|---|
| 1. 3-beta-(1'-piperidinylmethyl)-17a-methyl-17a-aza-D-homo-5-alpha-androstan-3-alpha-ol 17a-N-methoiodide | 0.209 | 90.72 | 23.41 | 20.71 | 19.5 | 14.9 |
| 2. 3-beta-(1'-piperidinylmethyl)-3-alpha-acetoxy-17a-methyl-17a-aza-D-homo-5-alpha-androstane 17a-N-methoiodide | 0.215 | 67.12 | 18.93 | 16.70 | −1.9 | −2.7 |
| 3. 3-beta-(1'-pyrrolidinylmethyl)-17a-methyl-17a-aza-D-homo-5-alpha-androstan-3-alpha-ol 17a-N-methoiodide | 0.340 | 45.66 | 26.71 | 25.55 | 0.7 | −7.3 |
| 4. 3-beta-(1'-hexamethyleneiminomethyl)-17a-methyl-17a-aza-D-homo-5-alpha-androstan-3-alpha-ol 17a-N-methoiodide | 0.119 | 94.60 | 18.40 | 15.40 | 22.1 | 10.1 |
| 5. 3-beta-(1'-pyrrolidinylmethyl)-3-alpha-acetoxy-17a-methyl-17a-aza-D-homo-5-alpha-androstane 17a-N-methoiodide | 0.337 | 72.52 | 82.65 | 81.59 | −1.5 | 0.7 |
| 6. 3-beta-(1'-hexamethyleneiminomethyl)-3-alpha-acetoxy-17a-methyl-17a-aza-D-homo-5-alpha-androstane 17a-N-methoiodide | 0.215 | 67.78 | 15.67 | 11.32 | 3.0 | −11.0 |
| 7. 3-beta-[1'-(4',4'-dimethyl-piperazinyl)methyl]-3-alpha-acetoxy-17a-dimethyl-17a-aza-D-homo-5-alpha-androstane diiodide | 0.102 | 83.26 | 23.67 | 19.80 | 22.8 | 8.2 |
| 8. 3-beta-diethylaminomethyl-17a-methyl-17a-aza-D-homo-5-alpha-androstan-3-alpha-ol 17a-N-methoiodide | 0.198 | 91.35 | 21.64 | 18.88 | −5.9 | −23.9 |
| 9. 3-beta-diethylaminomethyl-3-alpha-acetoxy-17a-methyl-17a-aza-D-homo-5-alpha-androstane 17a-N-methoiodide | 0.522 | 73.57 | 20.65 | 16.16 | −9.1 | −18.7 |
| 10. 3-beta-[1'-(1'-methylpiperidinyl)-methyl]-3-alpha-acetoxy-17a-dimethyl-17a-aza-D-homo-5-alpha-androstane diiodide | 0.142 | 100.64 | 32.06 | 23.45 | 2.3 | −0.5 |
| 11. 3-beta-N-(n-propyl)-N-(cyclopropyl-methyl)aminomethyl-17a-methyl-17a-aza-D-homo-5-alpha-androstan-3-alpha-ol 17-a-N-methoiodide | 0.213 | 72.58 | 14.88 | 11.76 | 5.0 | −7.1 |
| 12. 3-beta-[1'-(1'-methylpyrrolidinyl)-methyl]-3-alpha-acetoxy-17a-dimethyl-17a-aza-D-homo-5-alpha-androstane diiodide | 0.092 | 96.51 | 19.34 | 16.26 | 0.2 | −1.1 |

TABLE 3

STRUCTURE ACTIVITY RELATIONSHIP OF 3-ALPHA SUBSTITUTED AMINOMETHYL 3-SUBSTITUTED-OXY-17A-LOWER-ALKYL-17A-AZA-D-HOMO-5-ALPHA-ANDROSTANES IN DOG

| COMPOUNDS | eaDose mg/kg | 85% TW sec. | Duration min. | Recovery min. | HR % Ch | BP % Ch |
|---|---|---|---|---|---|---|
| 1. 3-alpha-(1'-pyrrolidinylmethyl)-17a-methyl-17a-aza-D-homo-5-alpha-androstan-3-beta-ol 17a-N-methoiodide | 0.423 | 92.34 | 19.96 | 15.41 | −2.5 | −7.1 |
| 2. 3-alpha-(1'-pyrrolidinylmethyl)-3-beta-acetoxy-17a-methyl-17a-aza-D-homo-5-alpha-androstane 17a-N-methoiodide | 0.240 | 56.27 | 13.96 | 11.95 | −2.4 | −3.4 |
| 3. 3-alpha-(1'-methylpyrrolidinyl)-methyl-3-beta-acetoxy-17a-dimethyl-17a-aza-D-homo-5-alpha-androstane diiodide | 0.253 | 85.45 | 29.86 | 24.33 | 2.0 | −1.0 |
| 4. 3-alpha-diethylaminomethyl-17a-methyl-17a-aza-D-homo-5-alpha-androstan-3-beta-ol 17a-N-methoiodide | 0.365 | 75.61 | 25.39 | 19.07 | 14.8 | −3.6 |
| 5. 3-alpha-diethylaminomethyl-3-beta-acetoxy-17a-methyl-17a-aza-D-homo-5-alpha-androstane 17a-N-methoiodide | 0.492 | 74.24 | 21.10 | 13.60 | −0.8 | −7.2 |
| 6. 3-alpha-(N-methyl-N,N-diethylamino)- | 0.155 | 111.39 | 37.77 | 34.77 | 3.1 | −2.0 |

TABLE 3-continued

STRUCTURE ACTIVITY RELATIONSHIP OF 3-ALPHA SUBSTITUTED AMINOMETHYL 3-SUBSTITUTED-OXY-17A-LOWER-ALKYL-17A-AZA-D-HOMO-5-ALPHA-ANDROSTANES IN DOG

| COMPOUNDS | eaDose mg/kg | 85% TW sec. | Duration min. | Recovery min. | HR % Ch | BP % Ch |
|---|---|---|---|---|---|---|
| methyl-3-beta-acetoxy-17a-dimethyl-17a-aza-D-homo-5-alpha-androstane diiodide | | | | | | |
| 7. 3-alpha-[1'-(4',4'-dimethyl-piperazinyl)methyl]-17a-dimethyl-17a-aza-D-homo-5-alpha-androstan-3-beta-ol diiodide | 0.261 | 99.08 | 33.65 | 25.43 | 10.2 | −8.1 |
| 8. 3-alpha-[1'-(4',4'-dimethyl-piperazinyl)methyl]-3-beta-acetoxy-17a-dimethyl-17a-aza-D-homo-5-alpha-androstane diiodide | 0.226 | 77.01 | 25.27 | 19.92 | 1.3 | −1.5 |

While a number of embodiments of this invention have been represented herein, it is apparent that the basic construction can be altered to provide other embodiments which utilize the invention without departing from the spirit and scope of the invention. All such modifications and variations are intended to be included within the scope of the invention as defined in the appended claims rather than the specific embodiments which have been presented by way of example.

I claim:

1. A compound represented by the Formula:

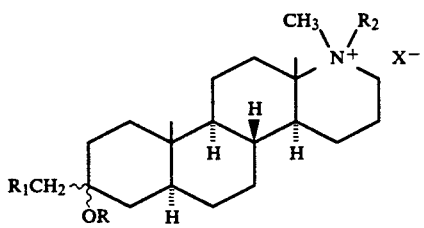

including optically active isomeric forms, and pharmaceutically acceptable acid addition salts thereof, wherein:

R is selected from the group consisting of hydrogen, lower-alkyl, lower-alkyl carbonyl, and di(lower-alkyl)amino carbonyl;

$R_1$ is selected from the group consisting of: di(lower-alkyl)substituted amino; lower-cycloalkyl lower-alkyl, lower-alkyl substituted amino; 1-piperidinyl; 1-pyrrolidinyl; 1-hexamethyleneimino; tri(lower-alkyl)substituted amino; 1-(1-methylpiperidinyl); and 1-(1-methylpyrrolidinyl), each lower-alkyl group having from 1 to 6 carbon atoms;

$R_2$ is a lower-alkyl group having from 1 to 4 carbon atoms;

$X^-$ is a pharmaceutically acceptable anion; and the symbol ∼ represents an alpha or beta configuration.

2. A compound according to claim 1, wherein R is lower-alkyl carbonyl.

3. A compound according to claim 1, wherein $R_1$ is selected from the group consisting of diethyl amine, N-(n-propyl)-N-(cyclopropyl methyl)amine, 1-pyrrolidinyl and 1-hexamethyleneimino.

4. A compound according to claim 1, which comprises 3-beta-(1'-pyrrolidinylmethyl)-17a-methyl-17a-aza-D-homo-5-alpha-androstan-3-alpha-ol 17a-N-methylbenzenesulfonate.

5. A compound according to claim 1, which comprises 3-beta-(1'-hexamethyleneiminomethyl)-17a-methyl-17a-aza-D-homo-5-alpha-androstan-3-alpha-ol 17a-N-methylbenzenesulfonate.

6. A compound according to claim 1, which comprises 3-beta-(1'-hexamethyleneiminomethyl)-3-alpha-acetoxy-17a-methyl-17a-aza-D-homo-5-alphaandrostane 17a-N-methylbenzenesulfonate.

7. A muscle relaxant composition comprising a pharmaceutically acceptable carrier and an effective amount of a compound represented by the formula:

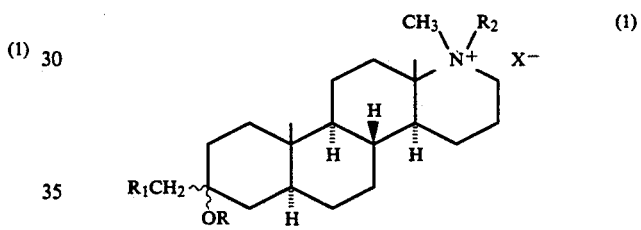

including optically active isomeric forms, and pharmaceutically acceptable acid addition salts thereof, wherein:

R is selected from the group consisting of hydrogen, lower-alkyl, lower-alkyl carbonyl, and di(lower-alkyl)amino carbonyl;

$R_1$ is selected from the group consisting of: di(lower-alkyl)substituted amino; lower-cycloalkyl lower-alkyl, lower-alkyl substituted amino; 1-piperidinyl; 1pyrrolidinyl; 1-hexamethyleneimino; tri(lower-alkyl)substituted amino; 1-(1-methylpiperidinyl); and 1-(1-methylpyrrolidinyl), each lower-alkyl group having from 1 to 6 carbon atoms;

$R_2$ is a lower-alkyl group having from 1 to 4 carbon atoms;

$X^-$ is a pharmaceutically acceptable anion; and the symbol ∼ represents an alpha or beta configuration.

8. A composition according to claim 7, wherein R is lower-alkyl carbonyl, and $R_1$ is selected from the group consisting of diethyl amine, N-(n-propyl)-N-(cyclopropylmethyl)amine, 1-pyrrolidinyl and 1-hexamethylenemine.

9. A composition according to claim 7, wherein the compound comprises 3-beta-(1'-hexamethyleneiminomethyl)-3-alpha-acetoxy-17a-methyl-17a-aza-D-homo-5-alpha-androstane 17a-N-methylbenzenesulfonate.

10. A method for producing muscle relaxation in a mammal comprising administering to the mammal an effective amount of a compound represented by the Formula:

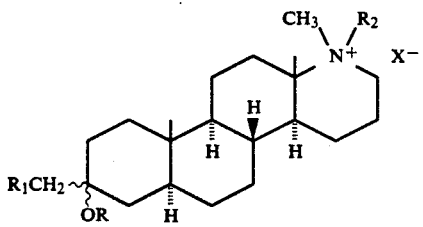

including optically active isomeric forms, and pharmaceutically acceptable acid addition salts thereof, wherein:

R is selected from the group consisting of hydrogen, lower-alkyl, lower-alkyl carbonyl, and di(lower-alkyl)amino carbonyl;

$R_1$ is selected from the group consisting of: di(lower-alkyl)substituted amino; lower-cycloalkyl lower-alkyl, lower-alkyl substituted amino; 1-piperidinyl; 1-pyrrolidinyl; 1-hexamethyleneimino; tri(lower-alkyl)substituted amino; 1-(1-methylpiperidinyl); and 1-(1-methylpyrrolidinyl), each lower-alkyl group having from 1 to 6 carbon atoms;

$R_2$ is a lower-alkyl group having from 1 to 4 carbon atoms;

$X^-$ is a pharmaceutically acceptable anion; and the symbol represents an alpha or beta configuration.

11. A method according to claim 10, wherein R is lower-alkyl carbonyl, and $R_1$ is selected from the group consisting of diethyl amine, N(n-propyl)-N-(cyclopropylmethyl)amine, 1-pyrrolidinyl and 1-hexamethylenemine.

* * * * *